(12) United States Patent
Vaishya

(10) Patent No.: US 9,973,867 B2
(45) Date of Patent: May 15, 2018

(54) MOISTURE RESISTANT HEADPIECES AND IMPLANTABLE COCHLEAR STIMULATION SYSTEMS INCLUDING THE SAME

(71) Applicant: Advanced Bionics AG, Staefa (CH)

(72) Inventor: Manish Vaishya, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days. days.

(21) Appl. No.: 14/796,157

(22) Filed: Jul. 10, 2015

(65) Prior Publication Data

US 2015/0382118 A1 Dec. 31, 2015

Related U.S. Application Data

(63) Continuation of application No. 13/977,549, filed as application No. PCT/US2012/020980 on Jan. 11, 2012, now Pat. No. 9,132,270.

(60) Provisional application No. 61/433,622, filed on Jan. 18, 2011.

(51) Int. Cl.
| | |
|---|---|
| *H04R 25/00* | (2006.01) |
| *A61N 1/375* | (2006.01) |
| *A61N 1/05* | (2006.01) |
| *A61N 1/36* | (2006.01) |
| *H01R 13/52* | (2006.01) |

(52) U.S. Cl.
CPC ......... *H04R 25/654* (2013.01); *A61N 1/0541* (2013.01); *A61N 1/36036* (2017.08); *A61N 1/375* (2013.01); *H04R 25/606* (2013.01); *H04R 25/608* (2013.01); *H01R 13/5202* (2013.01); *H01R 2201/12* (2013.01); *Y10T 29/49005* (2015.01)

(58) Field of Classification Search
CPC .. A61N 1/0541; A61N 1/36032; A61N 1/375; H04R 25/608; H04R 25/654
USPC ...................................... 607/57, 137; 29/594
See application file for complete search history.

(56) References Cited

U.S. PATENT DOCUMENTS

| | | | |
|---|---|---|---|
| 3,064,089 A | 11/1962 | Ward | |
| 3,976,848 A | 8/1976 | Estes | |
| 4,073,366 A | 2/1978 | Estes | |
| 4,447,677 A | 5/1984 | Miyahra et al. | |
| 4,570,746 A | 2/1986 | Das et al. | |
| 4,736,740 A | 4/1988 | Parker et al. | |
| 4,776,343 A * | 10/1988 | Hubbard | A61B 5/0215 600/486 |
| 4,870,952 A * | 10/1989 | Martinez | A61B 1/00117 362/572 |
| 4,953,215 A | 8/1990 | Weiss et al. | |
| 4,966,252 A | 10/1990 | Drever | |
| 4,987,597 A | 1/1991 | Haertl | |

(Continued)

FOREIGN PATENT DOCUMENTS

| | | |
|---|---|---|
| DE | 10104129 A1 | 8/2002 |
| DE | 102007027920 B3 | 12/2008 |

(Continued)

OTHER PUBLICATIONS

PCT Invitation to Pay Additional Fees and Results of Partial International Search dated Apr. 4, 2012 for PCT App. Ser. No. PCT/US2012/020980.

*Primary Examiner* — Christopher A Flory
(74) *Attorney, Agent, or Firm* — Henricks, Slavin & Holmes LLP

(57) ABSTRACT

Cochlear implant headpieces with improved moisture resistance.

12 Claims, 5 Drawing Sheets

(56) References Cited

U.S. PATENT DOCUMENTS

| | | | |
|---|---|---|---|
| 5,000,177 A * | 3/1991 | Hoffmann | A61N 1/3752 607/2 |
| 5,168,876 A * | 12/1992 | Quedens | A61B 5/0416 600/376 |
| 5,205,288 A * | 4/1993 | Quedens | A61B 5/0416 600/376 |
| 5,222,050 A * | 6/1993 | Marren | H04R 11/00 181/132 |
| 5,278,360 A | 1/1994 | Carbe et al. | |
| 5,365,595 A | 11/1994 | Li | |
| 5,530,763 A | 6/1996 | Aebi et al. | |
| 5,545,859 A | 8/1996 | Ullrich | |
| 5,627,802 A | 5/1997 | Langer | |
| 5,828,761 A | 10/1998 | Langer | |
| 6,018,585 A | 1/2000 | Akino et al. | |
| 6,061,457 A | 5/2000 | Stockhamer | |
| 6,071,527 A | 6/2000 | Tsujino et al. | |
| 6,093,144 A | 7/2000 | Jaeger et al. | |
| 6,104,816 A | 8/2000 | Downs, Jr. et al. | |
| 6,129,174 A | 10/2000 | Brown et al. | |
| 6,134,333 A * | 10/2000 | Flagler | H04R 25/654 181/130 |
| 6,164,409 A | 12/2000 | Berger | |
| 6,188,773 B1 | 2/2001 | Murata et al. | |
| 6,310,961 B1 | 10/2001 | Oliveira et al. | |
| 6,422,991 B1 | 7/2002 | Jaeger | |
| 6,427,018 B1 * | 7/2002 | Keliiliki | H04R 1/1066 381/370 |
| 6,505,076 B1 | 1/2003 | Tziviskos et al. | |
| 6,512,834 B1 | 1/2003 | Banter et al. | |
| 6,600,825 B1 | 7/2003 | Leysieffer | |
| 6,626,822 B1 | 9/2003 | Jaeger et al. | |
| 6,707,920 B2 | 3/2004 | Miller | |
| 6,795,562 B1 | 9/2004 | Gunnersen et al. | |
| 6,813,364 B1 | 11/2004 | Vonlanthen | |
| 6,879,696 B1 | 4/2005 | Vonlanthen | |
| 6,891,956 B2 | 5/2005 | Heerlein et al. | |
| 6,935,458 B2 | 8/2005 | Owens | |
| 7,013,016 B2 | 3/2006 | Wolf | |
| 7,065,224 B2 | 6/2006 | Cornelius et al. | |
| 7,136,496 B2 | 11/2006 | van Halteren et al. | |
| 7,283,640 B2 | 10/2007 | Karamuk | |
| 7,313,245 B1 * | 12/2007 | Shennib | A61F 11/08 128/864 |
| 7,322,930 B2 | 1/2008 | Jaeger et al. | |
| 7,433,482 B2 | 10/2008 | Wehner | |
| 7,630,772 B1 | 12/2009 | Walsh et al. | |
| 7,751,579 B2 | 7/2010 | Shulein et al. | |
| 7,793,756 B2 | 9/2010 | Karamuk | |
| 8,068,914 B1 | 11/2011 | Walsh et al. | |
| 8,155,748 B1 | 4/2012 | Walsh et al. | |
| 8,509,469 B2 * | 8/2013 | Miller, III | H04R 25/606 381/355 |
| 9,132,270 B2 | 9/2015 | Vaishya | |
| 2001/0036264 A1 | 11/2001 | Ito et al. | |
| 2002/0177883 A1 | 11/2002 | Tziviskos et al. | |
| 2003/0002706 A1 * | 1/2003 | Keliiliki | H04R 1/1066 381/381 |
| 2003/0219138 A1 | 11/2003 | Vonlanthen et al. | |
| 2004/0039245 A1 | 2/2004 | Jaeger et al. | |
| 2004/0161104 A1 | 8/2004 | DeMichele et al. | |
| 2004/0179709 A1 * | 9/2004 | Niederdraenk | H04R 1/086 381/322 |
| 2005/0018866 A1 | 1/2005 | Schulein et al. | |
| 2005/0077102 A1 * | 4/2005 | Banter | H04R 1/086 181/149 |
| 2005/0175203 A1 | 8/2005 | Karamuk | |
| 2006/0042865 A1 | 3/2006 | Berg et al. | |
| 2006/0114751 A1 | 6/2006 | Ferri et al. | |
| 2006/0140432 A1 | 6/2006 | Ueki | |
| 2006/0161255 A1 * | 7/2006 | Zarowski | H04R 25/606 623/10 |
| 2006/0215863 A1 | 9/2006 | Sauer | |
| 2006/0254851 A1 | 11/2006 | Karamuk | |
| 2007/0003081 A1 | 1/2007 | Ram et al. | |
| 2007/0003087 A1 | 1/2007 | Ram et al. | |
| 2007/0106344 A1 * | 5/2007 | Darley | H04R 25/60 607/55 |
| 2007/0113964 A1 | 5/2007 | Crawford et al. | |
| 2008/0095390 A1 | 4/2008 | Gebert et al. | |
| 2008/0165996 A1 | 7/2008 | Saito et al. | |
| 2008/0240479 A1 | 10/2008 | Linford et al. | |
| 2008/0298627 A1 | 12/2008 | Bonebright et al. | |
| 2009/0074220 A1 | 3/2009 | Shennib | |
| 2009/0147978 A1 | 6/2009 | Sauer et al. | |
| 2009/0154747 A1 * | 6/2009 | Vestergaard | H04R 25/654 381/325 |
| 2010/0092021 A1 * | 4/2010 | Wiskerke | H04R 1/08 381/364 |
| 2010/0128915 A1 | 5/2010 | Vonlanthen et al. | |
| 2010/0137941 A1 * | 6/2010 | Darley | H04R 25/60 607/55 |
| 2010/0137942 A1 * | 6/2010 | Darley | H04R 25/60 607/57 |
| 2010/0185254 A1 * | 7/2010 | Lindquist | A61N 1/0548 607/42 |
| 2010/0202648 A1 | 8/2010 | Dittli et al. | |
| 2010/0204747 A1 * | 8/2010 | Lindquist | A61N 1/3601 607/42 |
| 2010/0317936 A1 * | 12/2010 | Al-Ali | A61B 5/02444 600/323 |
| 2010/0319189 A1 | 12/2010 | Karamuk | |
| 2011/0029041 A1 * | 2/2011 | Wiskerke | H04R 25/606 607/57 |
| 2011/0046730 A1 * | 2/2011 | Meskens | A61N 1/36032 623/10 |
| 2011/0085688 A1 * | 4/2011 | Ram | H04R 1/086 381/325 |
| 2011/0319703 A1 * | 12/2011 | Wiskerke | H04R 25/30 600/25 |
| 2012/0041517 A1 | 2/2012 | Walsh et al. | |
| 2012/0163643 A1 * | 6/2012 | Vestergaard | H04R 25/654 381/325 |
| 2012/0219167 A1 * | 8/2012 | Yoong | H04R 25/654 381/325 |
| 2013/0035744 A1 * | 2/2013 | Wiskerke | H04R 1/08 607/57 |
| 2013/0243229 A1 * | 9/2013 | Shennib | H04R 25/602 381/323 |
| 2014/0169602 A1 * | 6/2014 | Walsh | A61N 1/36032 381/323 |
| 2015/0016648 A1 | 1/2015 | Kazemzadeh et al. | |

FOREIGN PATENT DOCUMENTS

| | | |
|---|---|---|
| EP | 0548580 B1 | 3/1996 |
| EP | 0835042 A2 | 4/1998 |
| EP | 0847227 A2 | 6/1998 |
| EP | 0920239 A2 | 6/1999 |
| EP | 1011295 A2 | 6/2000 |
| EP | 1060640 A1 | 12/2000 |
| EP | 1154583 A2 | 11/2001 |
| EP | 1439733 A1 | 7/2004 |
| FR | 2802374 A1 | 6/2001 |
| GB | 1099527 A | 1/1968 |
| GB | 2119203 A | 11/1983 |
| GB | 2369522 A | 5/2002 |
| JP | 62-290296 A | 12/1987 |
| JP | 07-015494 | 1/1995 |
| JP | 07-162984 | 6/1995 |
| JP | 2003-259474 | 9/2003 |
| JP | 2004-007330 | 1/2004 |
| JP | 2005-311917 | 11/2005 |
| JP | 2006-186422 | 7/2006 |
| JP | 2008-098743 | 4/2008 |
| JP | 2008-199225 | 8/2008 |
| WO | WO 9701258 | 1/1997 |
| WO | WO 9945744 | 9/1999 |
| WO | WO 0002419 A1 | 1/2000 |
| WO | WO 0045617 A2 | 8/2000 |
| WO | WO 03061335 A1 | 7/2003 |

(56) References Cited

FOREIGN PATENT DOCUMENTS

| WO | WO 2004075159 A2 | 9/2004 |
|---|---|---|
| WO | WO 2007005852 A2 | 1/2007 |
| WO | WO 2007109517 A1 | 9/2007 |
| WO | WO 2008116500 A1 | 10/2008 |
| WO | WO 2008154954 A1 | 12/2008 |
| WO | WO 2009138524 A2 | 11/2009 |
| WO | WO 2009146494 A1 | 12/2009 |
| WO | WO 2009152528 A1 | 12/2009 |
| WO | WO 2010009504 A1 | 1/2010 |
| WO | WO 2010116005 A2 | 10/2010 |
| WO | WO 2011015674 A1 | 2/2011 |

* cited by examiner

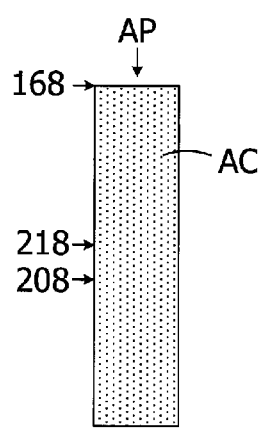
FIG. 12A
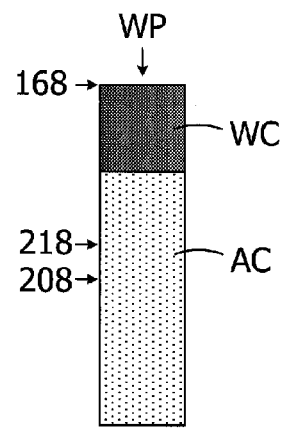
FIG. 12B
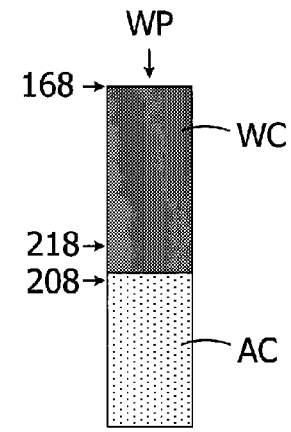
FIG. 12C
FIG. 13
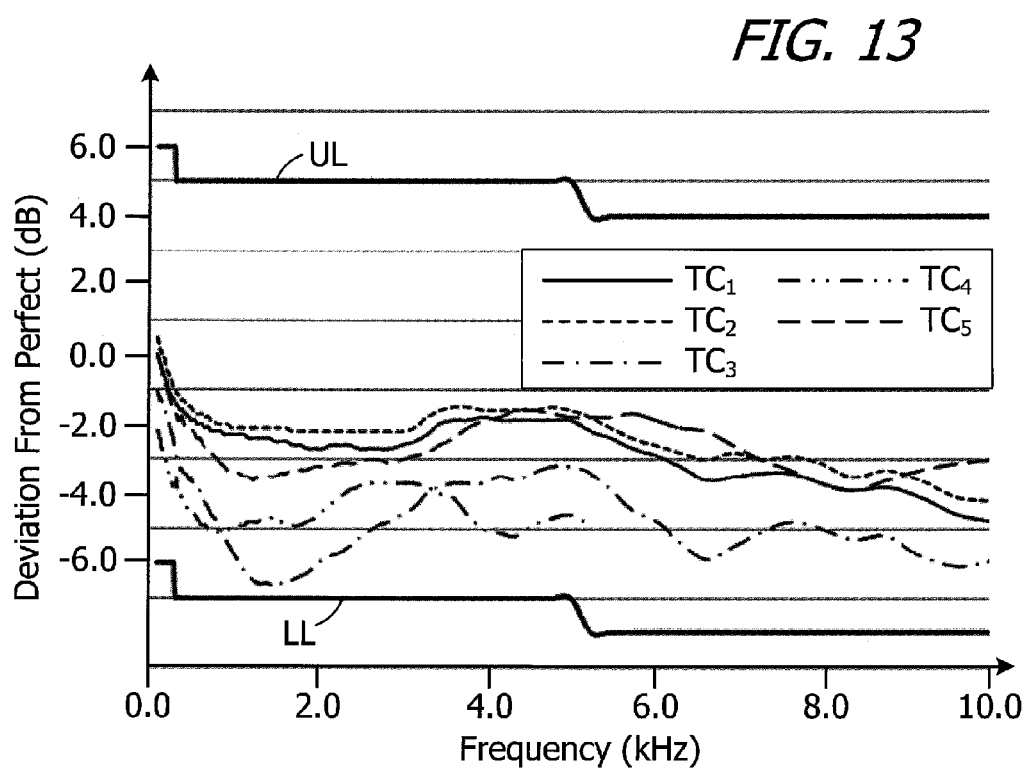

MOISTURE RESISTANT HEADPIECES AND IMPLANTABLE COCHLEAR STIMULATION SYSTEMS INCLUDING THE SAME

CROSS-REFERENCE TO RELATED APPLICATIONS

This application is a continuation of U.S. application Ser. No. 13/977,549, now U.S. Pat. No. 9,132,270, which has a 35 U.S.C. § 371(c) date of Jul. 23, 2013, which is the U.S. National Stage of PCT App. Ser. No. PCT/US2012/020980, filed Jan. 11, 2012, which claims priority to U.S. Prov. App. Ser. No. 61/433,622, filed Jan. 18, 2011. The content of each application is incorporated herein by reference in its entirety.

BACKGROUND

1. Field

The present disclosure relates generally to headpieces such as, for example, the headpieces in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound Processor With Remote Control" and incorporated herein by reference in its entirety.

As alluded to above, some ICS systems include an implantable device, a sound processor unit, and a microphone that is in communication with the sound processor unit. The implantable device communicates with the sound processor unit and, to that end, some ICS systems include a headpiece, with a microphone, that is in communication with both the sound processor unit and the implantable device. In one type of ICS system, the sound processor unit is worn behind the ear (a "BTE unit"), while other types of ICS systems have a body worn sound processor unit (or "body worn unit"). The body worn unit, which is larger and heavier than a BTE unit, is typically worn on the user's belt or carried in the user's pocket. One example of a conventional body worn unit is the Advanced Bionics Platinum Series body worn unit.

One issue associated with ICS systems is the moisture resistance of the headpiece. In particular, the present inventor has determined that it would be desirable to provide a headpiece that includes a microphone and is capable of being worn during activities such as swimming and bathing where the headpiece may be subjected to submersion in water, splashing and the like. The present inventor has also determined that the moisture resistance features of the headpiece should be configured in such a manner that the acoustic response is not substantially degraded, as compared to an identical microphone that is not within the headpiece.

SUMMARY

A cochlear implant headpiece in accordance with one embodiment of a present invention comprises a housing including a housing microphone aperture, a microphone carried within the housing and associated with the housing microphone aperture, a membrane between the housing microphone aperture and the microphone, and a cap, including a sound port and a shield over the sound port, configured to be positioned on the housing such that the sound port and shield are aligned with the housing microphone aperture. The present inventions also include cochlear stimulation systems with a cochlear implant, a sound processor, and such a headpiece.

A cochlear implant headpiece in accordance with one embodiment of a present invention comprises a housing, including an internal volume and a housing microphone aperture that extends to the internal volume, and a microphone carried within the housing internal volume and aligned with the housing microphone aperture. The internal volume is protected against particulate and moisture ingress to an extent greater than that required by IEC IP67. The present inventions also include cochlear stimulation systems with a cochlear implant, a sound processor, and such a headpiece.

A cochlear implant headpiece in accordance with one embodiment of a present invention comprises a housing, a transmitter, and a connector. The connector includes an electrically conductive barrel, an electrically conductive socket, an electrical insulator between the barrel and the socket, a first seal compressed between the barrel and the insulator, and a second seal compressed between the socket and the insulator. The present inventions also include cochlear stimulation systems with a cochlear implant, a sound processor, and such a headpiece.

A method of manufacturing a cochlear implant headpiece includes calculating the volume of the microphone aperture according to the formula $$V_{APERTURE} > (WP_{MAX}/AP)V_{MIC} - V_{MIC}, \text{ where}$$

$V_{APERTURE}$=microphone aperture volume, $WP_{MAX}$=water pressure at the predetermined maximum depth, AP=atmospheric pressure, and $V_{MIC}$=internal microphone volume.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIGS. 12A-12C are diagrammatic representations of the compression of an air column during submersion of a headpiece in accordance with one embodiment of a present invention.

FIG. 13 is a graph showing the acoustic response of a headpiece microphone in accordance with one embodiment of a present invention under various test conditions.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e., either sound or a perception of sound) to the hearing impaired as well as others who require such systems on a situational basis. One example of such a system is an ICS system where an external sound processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed.

Figure 1:
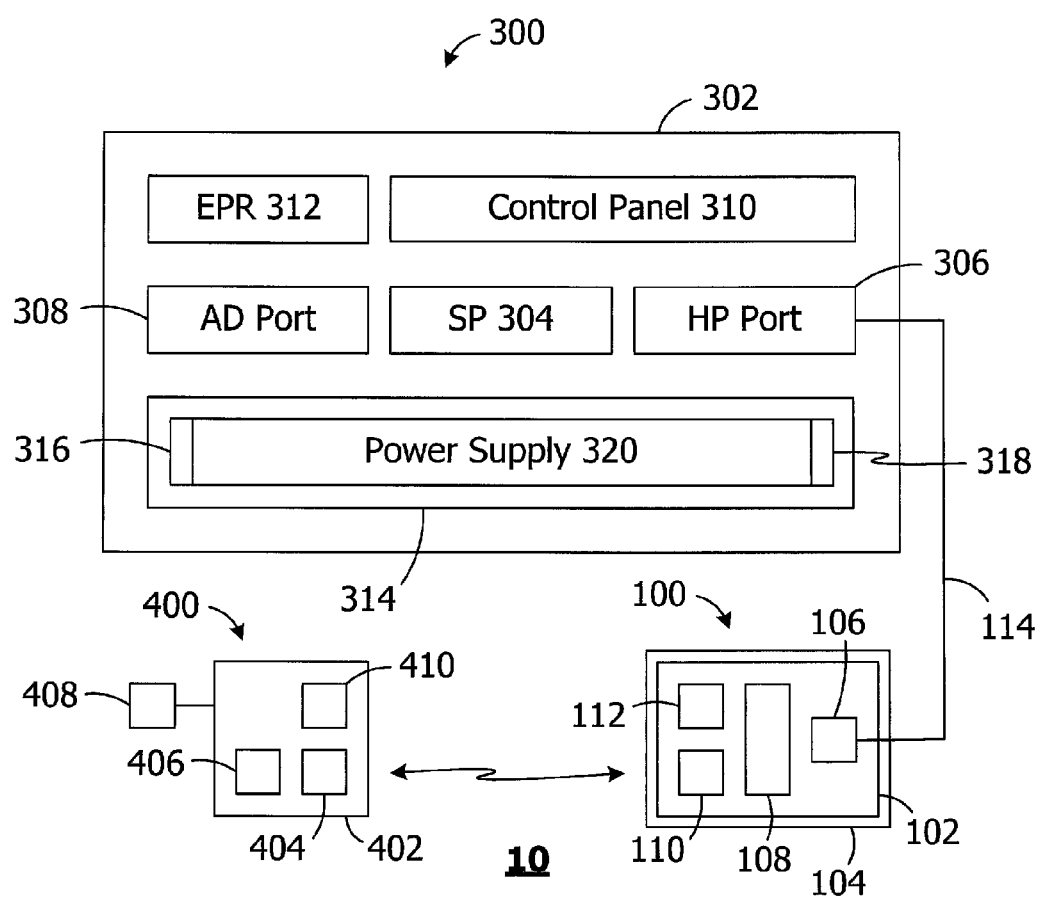
FIG. 1 is a functional block diagram of an ICS system in accordance with one embodiment of a present invention.
Figure 2:
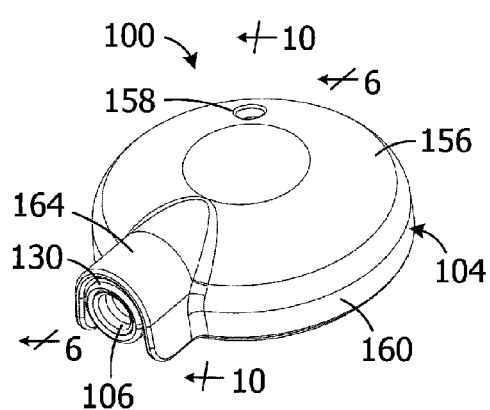
FIG. 2 is a perspective view of a headpiece in accordance with one embodiment of a present invention.
Figure 3:
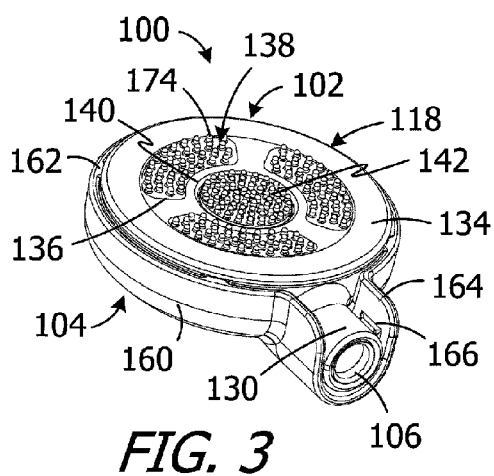
FIG. 3 is another perspective view of the headpiece illustrated in FIG. 2.
Figure 4:
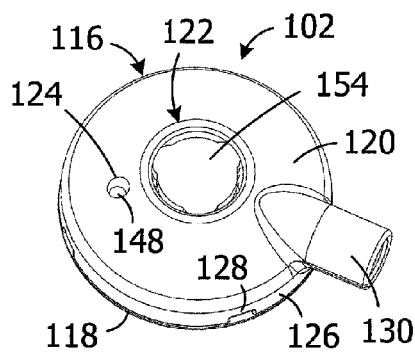
FIG. 4 is a perspective view of a portion of the headpiece illustrated in FIG. 2.

One example of an ICS system is generally represented by reference numeral 10 in FIG. 1. The system 10 includes a headpiece 100, a sound processor 300 and a cochlear implant 400.

The exemplary headpiece 100 includes a housing 102 and a removable cap 104, as well as various components, e.g., a RF connector 106, a microphone 108, an antenna (or other transmitter) 110 and a positioning magnet 112, that are carried by the housing. Additional details concerning the headpiece 100 are described below with reference to FIGS. 2-13. For example, the headpiece 100 may be configured such that it possesses particulate and moisture ingress protection that is superior to that represented by the International Electrotechnical Commission (IEC) IP67 rating, yet does not simply place the microphone within a sealed volume or otherwise shield the microphone in a way that would substantially degrade the acoustic response of the headpiece.

The exemplary sound processor 300 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310 (including, e.g., a volume knob and program switch), a Euro Plug receptacle 312 (for a Euro Plug such as that associated with the Phonak MLxi FM receiver), and a power supply receptacle 314 with electrical contacts 316 and 318 for a removable battery or other removable power supply 320 (e.g., rechargeable and disposable batteries or other electrochemical cells). A power button (not shown) may also be carried on the housing 302. The headpiece port 306 and auxiliary device port 308 may be connected to the sound processor circuitry 304 by way of, for example, a signal splitter/combiner (not shown) such as that found in the Platinum Signal Processor body worn unit from Advanced Bionics.

The headpiece 100 in the exemplary ICS system 10 may be connected to the headpiece port 306 by a cable 114. In at least some implementations, the cable 114 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques.

The exemplary cochlear implant 400 includes a housing 402, an antenna 404, an internal processor 406, a cochlear lead 408 with an electrode array, and a positioning magnet (or magnetic material) 410. The transmitter 110 and receiver 404 communicate by way of electromagnetic induction, radio frequencies, or any other wireless communication technology. The positioning magnet 112 and positioning magnet (or magnetic material) 410 maintain the position of the headpiece antenna 110 over the cochlear implant antenna 404.

During use, the microphone 108 picks up sound from the environment and converts it into electrical impulses, and the sound processor 300 filters and manipulates the electrical impulses and sends the processed electrical signals through the cable 114 to the antenna 110. Electrical impulses received from an auxiliary device are processed in essentially the same way. The receiver 404 receives signals from the antenna 110 and sends the signals to the cochlear implant internal processor 406, which modifies the signals and passes them through the cochlear lead 408 to the electrode array. The electrode array may be wound through the cochlea and provides direct electrical stimulation to the auditory nerves inside the cochlea. This provides the user with sensory input that is a representation of external sound waves which were sensed by the microphone 108.

The exemplary sound processor 300 may be carried by the user in a variety of ways. By way of example, but not limitation, the sound processor 300 may be carried in the user's pocket, secured to a belt with a belt clip that is either part of housing 106 or a separate carrier, or placed in a harness that is configured to be worn by a small child.

Turning to FIGS. 2-5, and as noted above, the exemplary headpiece 100 includes a housing 102 and a removable cap 104 that may be secured to the housing. The housing 102 has a main portion 116 and a cover 118 that may be secured to the main portion in the manner described in greater detail below with reference to FIG. 6. The exemplary housing main portion 116 has a top wall 120, a cup 122 for the magnet 112, a housing microphone aperture 124, a side wall 126 with a plurality of latch indentations 128, and a connector tube 130 for the connector 106. The exemplary cover 118 has a side wall 132 and a bottom wall 134 that extends slightly beyond the side wall. The bottom wall 134 includes a plurality of apertures 136 for friction pads 138 that are molded into the bottom wall (note FIG. 6), as well as a recess 140 for a friction pad 142 that is adhered to the bottom wall. The configurations of the housing main portion 116 and cover 118 are such that the inner surface of the main portion side wall 126 abuts the outer surface of the cover side wall 132 and the end of the main portion side wall abuts the cover bottom wall 134 (note FIG. 6) when the housing 102 is in the assembled state.

The exemplary housing 102 has an internal volume 144 (FIG. 5), defined by the main portion 116 and cover 118, in which the microphone 108, a microphone holder 146, a membrane 148 and a printed circuit board (PCB) 150 are positioned. In the illustrated implementation, all of electronic components (with the exception of the microphone 108 and connector 106) are carried on the PCB 150. The connector 106 is positioned in the connector tube 130 such that the connector wires 152 may be connected to the PCB 150 by, for example, solder. The configuration of the connector 106, and the manner in which it is mounted within the connector tube 130, are discussed below with reference to FIGS. 6-8. The microphone holder 146 is positioned in the housing 102 such that the microphone wires 153 may be connected to the PCB 150 by, for example, solder. On the other side of the top wall 120 and outside the internal volume 144, one or more spacers 154 are carried within the cup 122 to hold the magnet 112 in place.

The cap 104 in the illustrated embodiment may be connected to and then removed from the housing 102, i.e., the cap may be removably connected to the housing. As used herein, "removably connected" means that, once connected, the cap 104 will remain on the housing 102 under normal use conditions, but can be removed from the housing without destruction of the housing, the cap and/or the instrumentality that secures the two to one another. Although one exemplary connector configuration is illustrated in FIGS. 2-5, others may be employed. In other implementations, single-use caps may be provided. A "single-use connection" is a connection where, once connected, the cap will remain on the housing under normal use conditions, but can be removed from the housing without damage to the housing. Damage or destruction to the cap and/or the instrumentality that secures the cap to the housing is possible with a single-use connection.

Referring to FIGS. 2-5, the exemplary cap 104 includes a top wall 156 with a sound port 158, a side wall 160 with a plurality of latches 162, and a connector hood 164 with a pair of latches 166. The cap 104 also carries a shield 168 (see also FIGS. 9-11). The respective configurations of the housing 102 and cap 104 allow the cap to be snap fit onto the housing and removed from the housing. In particular, the cap latches 162 will be aligned with the housing latch indentations 128 when the housing 102 and cap 104 are oriented in the manner illustrated in FIG. 5. The distance between the inner surfaces of the hood latches 166 is less than the diameter of the connector tube 130, and the distance between the hood top inner surface 170 (FIG. 9) is greater than the diameter of the connector tube. The cap 104 is also somewhat flexible. Thus, as the cap 104 is pressed onto the housing 102, the cap side wall 160 and hood 164 will bow outwardly as the latches 162 and 166 slide along the housing side wall 126 and connector cover 130. When the cap 104 reaches the position illustrated in FIGS. 2 and 3, the resilience of the cap will force the latches 162 into the latch recess 128 and the hood latches 166 against the surface of the connector cover 130, thereby latching the cap to the housing 102. The cap 104 may be removed by pulling the cap at the end of the hood 164 in the direction of arrow A.

Figure 5:
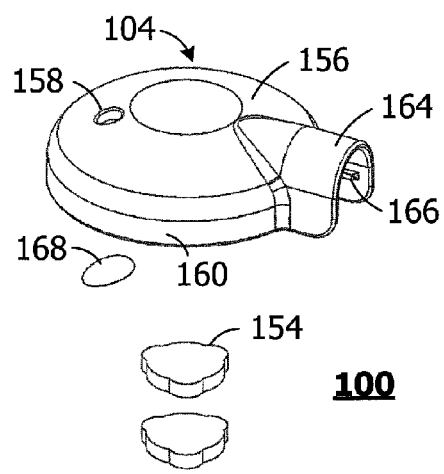
FIG. 5 is an exploded view of the headpiece illustrated in FIG. 2.
Figure 5:
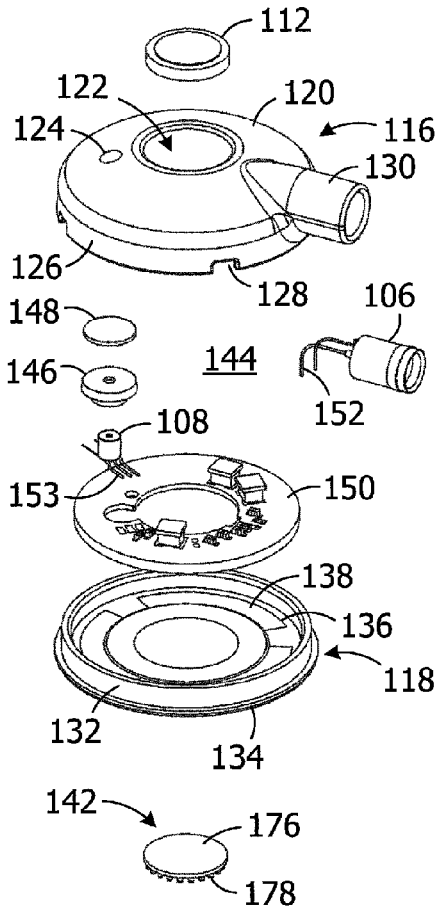
Figure 6:
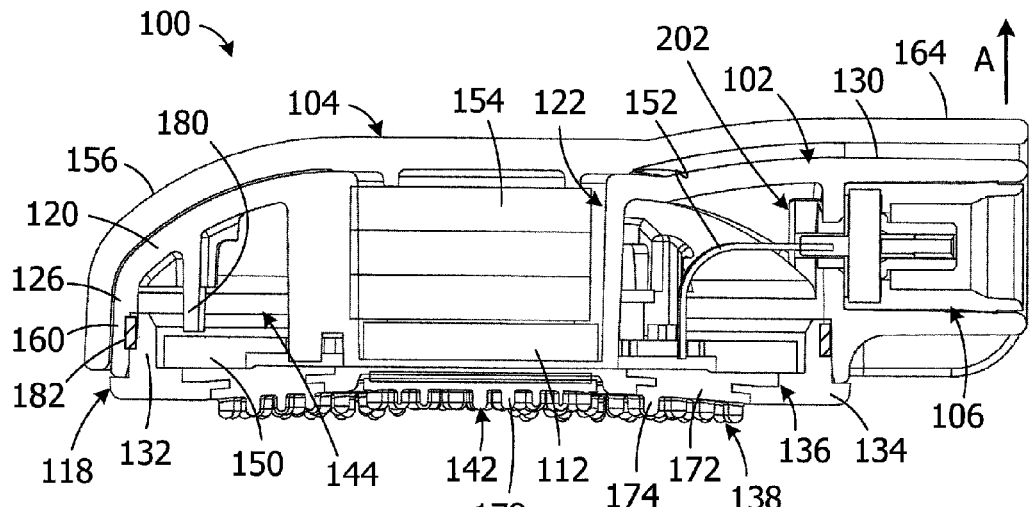
FIG. 6 is a section view taken along line 6-6 in FIG. 2.

The exemplary friction pads 138 and 142 facilitate retention of the headpiece in the desired location over hair and sweat. As illustrated in FIG. 6, the friction pads 138 include a base 172 and a plurality of spaced flexible bumps 174. The respective configurations of the apertures 136 and the bases 172 are such that, once the friction pads 138 have been overmolded into the housing cover bottom wall 134, they will be mechanically interlocked with the housing cover 118. The bases 172 also form seals that prevent ingress of particles and moisture through the apertures 136 to a level superior to that represented by the IEC IP67 standard. Referring to FIG. 5, the friction pad 142 includes a base 176 and a plurality of flexible bumps 178. The bumps 174 and 178 define multiple low- and zero-pressure channels that allow blood to flow in nearly every part of the skin and tissue underneath the headpiece 100. The bumps 174 and 178 can also resiliently deform and flex independently, which allows the headpiece 100 to conform to the contour of the skin and to dynamically conform to the skin with minor changes of the skin. Although the exemplary bumps 174 and 178 have a right cylindrical base and a hemispherical tip, other shapes may be employed. By way of example, but not limitation, other bumps may have a conical base and a flat tip, a conical base and a concave tip, a right cylindrical base and a conical tip, a regular pyramidal base extending to a pointed tip, a tapered rectangular base that is truncated to form a flat rectangular tip, or a rectangular base tapering to a wedge-shaped tip.

Suitable materials for the pads 138 and 142 include, but are not limited to, thermoplastic elastomers (TPE) such as SANTOPRENE TPE or VERSOLLAN TPE, or a silicone rubber such as SILASTIC silicone elastomer. The material may have a durometer of between 20 and 70 Shore A, and may be about 50 Shore A in some embodiments.

In the illustrated implementation, the base 176 is secured to the recess 140 in the housing cover bottom wall 134 with adhesive or other suitable instrumentalities. In other implementations, a second magnet (not shown) may be secured to the recess 140 in place of the friction pad 142 for patients that require a higher retention force.

Figure 7:
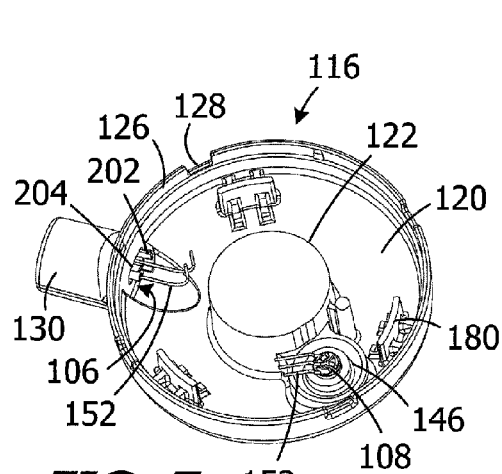
FIG. 7 is a perspective view of a portion of the headpiece illustrated in FIG. 2.

Turning to FIG. 7, the exemplary housing main portion 116 includes a plurality of support posts 180. The support posts 180 are used to mount and locate the PCB 150 within the housing.

A variety of aspects of the exemplary headpiece 100 contribute to the aforementioned particulate and moisture ingress protection that is superior to that represented by the IEC IP67 standard. For example, and referring to FIG. 6, the housing main portion 116 may be secured to the cover 118 by way of a robust joint 182. Suitable methods of forming the joint 182 include, but are not limited to, ultrasonic welding. Here, the joint 182 is formed from the main portion and cover material and no additional connective instrumentalities (e.g., adhesives) are employed. The joint 182 will prevent ingress of moisture into the internal volume 144 by way of the main portion 116 and cover 118 interface, thereby preventing damage to the PCB 150, at submersion depths of 3.0 m or more.

With respect to dimensions, the headpiece 100 may be any size suitable for the intended application. In one exemplary embodiment, and referring to FIG. 2, the length (measured along line 6-6) of the exemplary headpiece 100 may about 40 mm or less, the width (perpendicular to the length) may be about 35 mm or less, and the height may be about 14 mm or less. The housing 102 and cap 104 may be formed from any suitable materials. By way of example, but not limitation, the housing 102 and cap 104 may be formed from a polycarbonate/polyester compound such as XYLEX polycarbonate/polyester compound.

Figure 8:
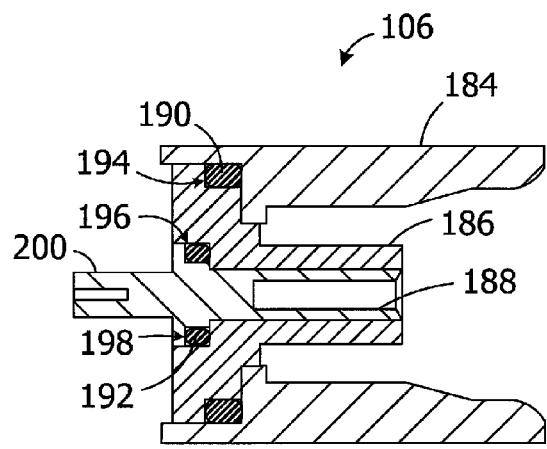
FIG. 8 is a section view of a connector in accordance with one embodiment of a present invention.
Figure 9:
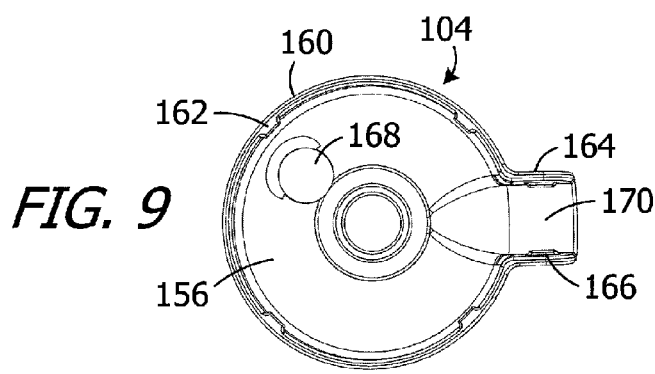
FIG. 9 is a plan view of a portion of the headpiece illustrated in FIG. 2.

The connector 106 may also be configured so as to prevent particulate and moisture ingress beyond that required by an IP67 rating and, as discussed in greater detail below, to at least an IP68 rating. Turning to FIG. 8, the exemplary connector 106 includes a barrel 184, an electrical insulator 186 and a socket 188. The barrel 184 and socket 188 may be formed from suitable electrically conductive materials such as, for example, beryllium copper or brass, while the insulator 186 may be formed from a dielectric material such as, for example, polytetrafluoroethylene (PTFE). The barrel 184 has a cylindrical outer surface and the connector tube 130 has a correspondingly sized inner surface, as shown in FIG. 6. With respect to waterproofing, the connector 106 may be provided with seals between the interfaces between the barrel 184, insulator 186 and socket 188 to prevent ingress of moisture into the internal volume 144 by way of the interfaces between the barrel, insulator and socket. In the illustrated embodiment, a pair of o-ring seals 190 and 192 are compressed between the barrel 184, insulator 186 and socket 188. The insulator 186 and socket 188 are provided with recesses 194, 196 and 198 to accommodate the seals 190 and 192 as well as to control the location and compression of the seals. Suitable materials for the seals 190 and 192 include, but are not limited to, silicone rubber. The compression of the seals 190 and 192 may be such that the thickness is about 10-20% less than the uncompressed diameter, and is about 15% less than the uncompressed diameter in the illustrated embodiment. Connector posts 200 and 202 for wires 152 are also provided. The connector post 202 and associated wire 152 are shown spaced apart from one another in FIG. 7 for clarity.

With respect to assembly of the connector 106 into the housing 102, and referring to FIG. 7, the exemplary housing main portion 116 includes an opening 204 on the inner surface of the side wall 126 that extends into the connector tube 130. During assembly, the connector 106 is pushed into the connector tube 130 through the open end. The opening 204 is then sealed, e.g., with UV activated epoxy (not shown).

Figure 10:
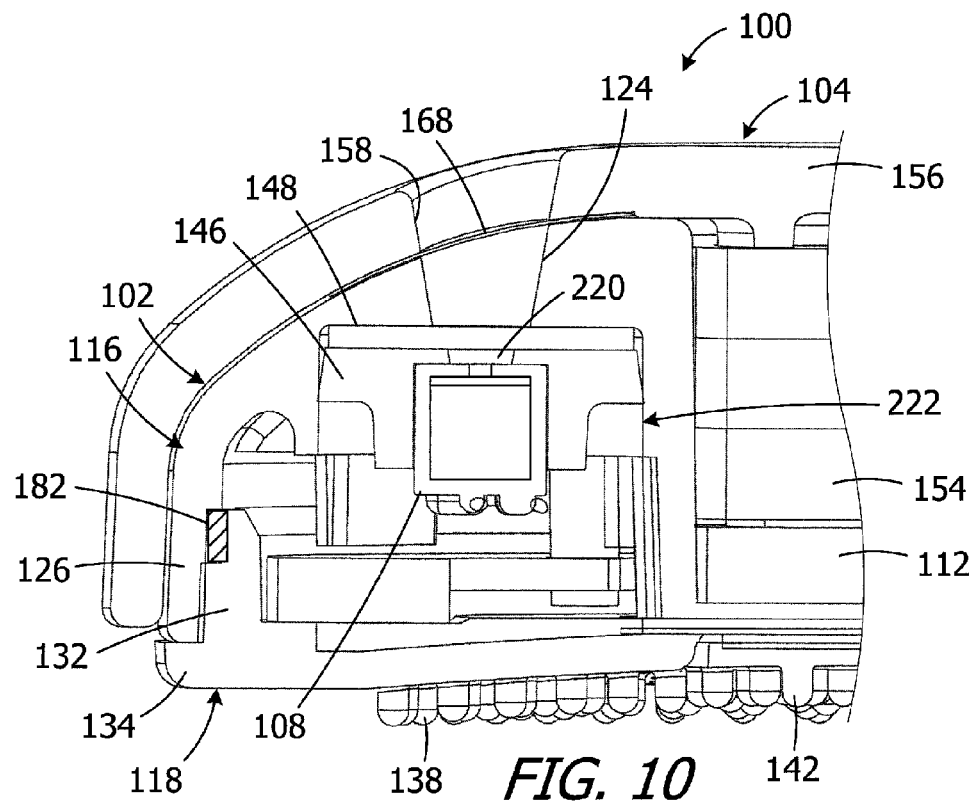
FIG. 10 is a section view taken along line 10-10 in FIG. 2.
Figure 11:
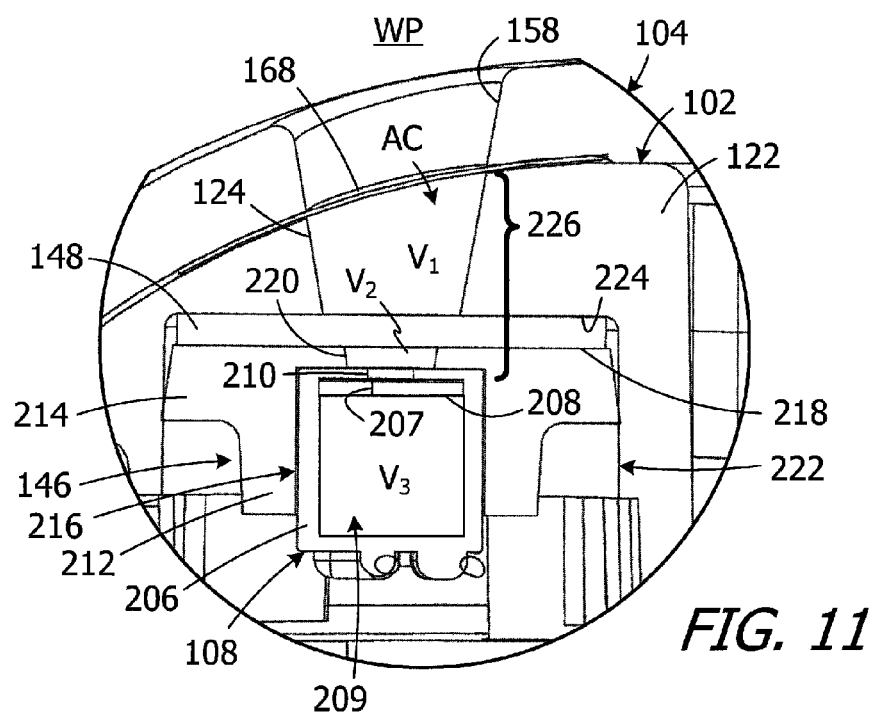
FIG. 11 is an enlarged view of a portion of FIG. 10.

Turning to FIGS. 10 and 11, the exemplary microphone 108 includes, among other conventional microphone structures, a housing 206, a diaphragm 208 that provides the acoustic response, an open region 209 behind the diaphragm, and a sound aperture 210. Electrical circuitry (not shown) occupies a portion of the open region 209. The microphone diaphragm 208 is a thin structure (e.g., about 0.005 inch thick) that includes a small hole 207 which may be, for example, about 15 μm in diameter. The diaphragm hole 207 insures that the pressure is equal on both sides of the microphone diaphragm 208 so that the acoustic response is similar at different barometric conditions. The open region 209 is the volume within the housing 206 not occupied by microphone components. The exemplary microphone holder 146 has a relatively narrow portion 212, a relatively wide portion 214, a recess 216 for the microphone 108, a top surface 218 and a holder aperture 220. The exemplary housing 102 includes a mounting recess 222 in the main portion 116 that is configured to receive the microphone holder 146. The configurations of the housing 102, microphone 108 and microphone holder 146 are such that microphone sound aperture 210 and holder aperture 220 are aligned. The membrane 148 is positioned between the microphone holder top surface 218 and the end wall 224 of the mounting recess 222.

It should be noted here that, in the illustrated embodiment, the headpiece microphone aperture 226 (FIG. 11) consists of the housing microphone aperture 124, the microphone sound aperture 210, the microphone holder aperture 220 and the pores in the cylindrical portion of the membrane 148 that extends from the housing microphone aperture 124 to the holder aperture 220. In other words, there is no wall or other non-porous structure between the environment and the microphone diaphragm 208 that would interfere with sound waves in addition to preventing moisture ingress. The respective configurations of the housing 102 and the cap 104 are such that the housing microphone aperture 124 and the cap sound port 158 are aligned with one another and the shield 168 is positioned therebetween. As such, air, sound and moisture may pass through the cap 104 and into the microphone aperture 226.

Passage of moisture through the hole 207 in the microphone diaphragm 208 and into the interior of the microphone would damage or destroy the microphone 108, while dust and other particulates would degrade the acoustic response. Accordingly, the exemplary headpiece 100 is configured to protect the microphone diaphragm 208 from moisture without adversely effecting the acoustic response of the headpiece.

For example, the exemplary membrane 148 is a hydrophobic membrane that protects against water ingress into the microphone 108 at relatively low pressures, e.g., in the shower, or during submersion at depths up to 0.5 m where the water pressure is about 0.05 bar. Suitable materials for the membrane 148 include, but are not limited to, a hydrophobic-treated polyethylene sheet from Porex Technologies (part no. XM-18505) that is about 0.45+/−0.05 mm thick.

The exemplary shield 168 is an acoustic hydrophobic membrane that is configured to prevent dust, soap, oils, and other relatively large particles and drops (i.e. 30 microns or larger) from reaching membrane 148. The shield 168 will not preclude water from reaching the membrane 148 (e.g., during submersion), but will prevent air turbulence between the shield and membrane 148. The significance of turbulence prevention is discussed below. Suitable materials for the shield 168 include, but are not limited to, PETEX hydrophobic acoustic material (part no. 145-27 07-27/16), which is a 1:2 twill weave of PET monofilament fibers. It should also be noted that the shield 168 is a non-permanent, serviceable portion of the headpiece 100 and may be readily removed from the housing 102, along with the cap 104, and replaced as necessary or desired. In the illustrated embodiment, the shield 168 is a permanently secured to the cap 104 with adhesive and the shield will be replaced with the cap. The shield 168 is also robust enough to be cleaned by wiping the shield with a cloth when the cap 104 is removed from the housing.

The exemplary headpiece 100 may also be configured to maintain a column of air over the microphone 108 that will prevent moisture from reaching the microphone diaphragm 208 during submersion of the headpiece up to a predetermined maximum submersion depth (e.g., submersion up to a depth of 3.0 m). The column of air will not, however, interfere with the transmission of sound waves to the microphone diaphragm 208 or otherwise degrade the acoustic response of the headpiece as would positioning a non-porous cover between the microphone and the environment.

More specifically, and referring to FIG. 11, an air column AC extends (prior to submersion) from shield 168, through the housing microphone aperture 124, the pores in the cylindrical portion of the membrane 148 that extends from the microphone aperture 124 to the microphone holder aperture 220, the microphone holder aperture 220 itself, to the bottom end (in the illustrated orientation) of the internal region 209 of the microphone 108. The air column AC will be compressed by water that passes through the shield 168 when the headpiece 100 is submerged. The amount of compression is a function of the water pressure WP which, in turn, is a function of the submersion depth. The relationship of the respective volumes $V_1$ (i.e., the volume within of the housing microphone aperture 124 and the pores of the aligned cylindrical portion of the membrane 148), $V_2$ (i.e., the volume of the microphone sound aperture 210 and microphone holder aperture 220) and $V_3$ (i.e., the volume of the region 209 behind the microphone diaphragm 208) may be selected such that water will not reach the microphone diaphragm 208 during submersions up to a predetermined depth. The total volume of the air in the air column AC prior to submersion must be such that, when compressed by the water at the predetermined maximum submersion depth, the compressed volume of the air column will be greater than $V_3$ in order to insure that water does not reach the microphone diaphragm 208. Put another way, volumes $V_1$ and $V_2$ together define an aperture volume, which is the portion of the air column AC on the housing side of the microphone diaphragm 208, and the volumetric reduction of the air column may not exceed the aperture volume.

One example of the above-described volumetric relationship is diagrammatically illustrated in FIGS. 12A-12C. The locations of the shield 168, the microphone diaphragm 208 and the microphone holder top surface 218 are shown for perspective. The air column AC is shown in FIG. 12A prior to submersion and exposed to atmospheric pressure AP. The air column AC has an uncompressed volume at atmospheric pressure $VAC_{AP} = V_1 + V_2 + V_3$. After the headpiece 100 has been submerged, water will enter the housing microphone aperture 124 (FIG. 11), pass through the shield 168 and form a water column WC. FIG. 12B shows the air column AC being compressed by the water pressure WP when the headpiece 100 is submerged to a depth that is less than the predetermined maximum depth. The water pressure WP will increase as the depth of the submersion increases. At the predetermined maximum submersion depth, the water pressure $WP_{MAX}$ is such that the volume of the compressed air column $VAC_{COMP}$ will be slightly greater than volume $V_3$ (FIG. 11), thereby preventing the water column WC from reaching the microphone diaphragm 208.

The relationship of volumes $V_1$, $V_2$ and $V_3$ is related to Boyle's gas law, which states that the product of gas pressure and gas volume is a constant. Thus, $$VAC_{AP} \times AP = VAC_{COMP} \times WP_{MAX};\text{ and}$$

$$VAC_{COMP} = VAC_{AP} \times (AP/WP_{MAX}).$$

For example, atmospheric pressure is 100 kPa and water pressure at a depth of 3.0 m is 130 kPa. Thus, for a maximum submersion depth of 3.0 m, $VAC_{COMP} = VAC_{AP} \times (100/130) = (V_1 + V_2 + V_3)(100/130)$. However, given that $VAC_{COMP}$ should be greater than $V_3$ in order to prevent damage to the microphone, the equation $(V_1 + V_2) > 0.3 V_3$ defines the volumetric relationship when the predetermined maximum submersion depth is 3.0 m. The relationship of $(V_1 + V_2)$, which is the aperture volume on the housing side of the microphone diaphragm 208, to $V_3$, which is the volume on the other side of the microphone diaphragm, will be different for different maximum submersion depths. Thus, more generally, the equation $(V_1 + V_2) > (WP_{MAX}/AP)V_3 - V_3$ defines a volumetric relationship whereby the air column will prevent water from reaching the microphone diaphragm 208.

Additionally, for best performance, the air column AC should not be subjected to turbulence during submersion that could result is some of the air escaping from the column and being replaced with water. The shield 168 reduces the likelihood that there will be turbulence sufficient to result in air escape. Alternatively, or in addition, horizontal and/or vertical baffles (not shown) may be provided in the air column AC in some embodiments to further prevent turbulence in the air column.

The headpiece described above was also tested under various conditions. Test results, which are presented in graph form in FIG. 13, show that the headpiece 100 provides ingress protection that is superior to the IEC IP67 standard without substantially degrading acoustic response. An IP67 rating indicates that the device is dust-tight and that internal structures are protected against moisture ingress at immersion depths of 15 cm to 1 m for 30 minutes.

The acoustic response of a microphone 108 mounted in a headpiece 100 in the manner described above was measured at frequencies ranging from 150 Hz to 10 kHz under a variety of test conditions. The goal prior to testing was no more than +/−6 dB deviation from a theoretically perfect microphone after being subjected to all test conditions, as shown by the upper limit UL and lower limit LL plots on the graph illustrated in FIG. 13. Headpiece acoustic response, prior to submersion testing, within +/−6 dB deviation from a theoretically perfect microphone is acoustic response that is not substantially degraded. The ingress of water into the microphone 108 would result in deviation outside this range and, accordingly, it may be assumed that acoustic response within +/−6 dB deviation from a theoretically perfect microphone indicates that water did not reach the microphone diaphragm 208.

A single headpiece 100 was employed for all of the tests discussed below. Under test condition $TC_1$, the acoustic response of the microphone 108 in a new, dry headpiece 100 was tested. In other words, test condition $TC_1$ is simply used to confirm that the microphone 108 is not defective and that the acoustic response of the headpiece is within the acceptable, not substantially degraded, range. For test condition $TC_2$, which is referred to herein as the "IP68 test," the same headpiece 100 was submerged in water at a depth of 3 m for 30 minutes. The headpiece 100 was then fully dried and the acoustic response of the microphone 108 in the headpiece tested. Test conditions $TC_3$ to $TC_5$ simulate the exposure to water and other contaminants that a headpiece 100 could experience over the course of three years, and are substantially tougher than the IP68 test. Test condition $TC_3$ is representative of the amount of direct exposure to a shower stream that the headpiece will experience, assuming that the wearer takes one shower a day for three years. Here, the headpiece 100 was subjected to 27 cycles of exposure to a direct shower stream. Each cycle consisted of 30 minutes of direct exposure to the shower stream followed by shaking, wiping and full drying (e.g., 1-8 hours in a desiccant dryer). The acoustic response of the microphone 108 in the headpiece 100 was tested after the last cycle. Test condition $TC_4$ is representative of conditions that would be experienced in a bathtub environment over the course of three years. Here, the headpiece 100 was subjected to 9 cycles of submersion to a depth of 0.05 m in bath water including soap, shampoo and lotion. Each cycle consisted of 1 hour of submersion followed by shaking, wiping and full drying (e.g., 1-8 hours in a desiccant dryer). The acoustic response of the microphone 108 in the headpiece 100 was tested after the last cycle. Test condition $TC_5$ is representative of the conditions that could be experienced by a headpiece worn by a person who swims twice a week. Here, the headpiece 100 was subjected to 5 cycles of submersion to a depth of 1.0 m in pool water including chlorine. Each cycle consisted of 30 minutes of submersion followed by shaking, wiping and full drying (e.g., 1-8 hours in a desiccant dryer). The acoustic response of the microphone 108 in the headpiece 100 was tested after the last cycle.

As illustrated in FIG. 13, the acoustic response of the microphone 108 in the headpiece 100 was within the +/−6 dB deviation range for all test conditions. Thus, these tests show that there was no water ingress into the microphone 108 under test conditions $TC_2$ to $TC_5$.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. Additionally, the inventions described herein are also applicable to BTE sound processors. The present inventions also include systems including headpieces in accordance with description above and claims below in combination with a sound processor and/or a cochlear implant. It is intended that the scope of the present inventions extend to all such modifications and/or additions and that the scope of the present inventions is limited solely by the claims set forth below.

I claim:

1. A cochlear implant headpiece, comprising:
a housing including a housing microphone aperture;
a microphone, carried within the housing and associated with the housing microphone aperture, including a microphone housing, a sound aperture, an open region defining a volume within the microphone housing, and a diaphragm between the sound aperture and the open region;
a microphone holder having an aperture with a volume that is aligned with the microphone sound aperture;
a membrane, having pores with volumes, positioned between the housing microphone aperture and the microphone such that at least a portion of the membrane is aligned with the housing microphone aperture; and
a cap, including a sound port and a shield over the sound port, configured to be positioned on the housing such that the sound port and shield are aligned with the housing microphone aperture;
wherein the housing microphone aperture, the portion of the membrane that is aligned with the housing microphone aperture, the microphone holder aperture, and the microphone sound aperture together define a combined volume that is greater than (0.3)×(the volume of the microphone open region); and
wherein the housing and cap are configured such that they will be removably connected to one another when the cap is positioned on the housing.

2. A cochlear implant headpiece as claimed in claim 1, wherein the membrane comprises a hydrophobic membrane.

3. A cochlear implant headpiece as claimed in claim 2, wherein the hydrophobic membrane is configured to prevent water passage at water pressures up to about 0.05 bar.

4. A cochlear implant headpiece as claimed in claim 1, wherein the shield is configured to prevent passage of particles that are at least 30 microns in diameter.

5. A cochlear implant headpiece as claimed in claim 4, wherein the shield is configured to allow passage of water.

6. A cochlear implant headpiece as claimed in claim 1, wherein
the housing includes a main portion and a cover secured to one another by a joint formed from material from the main portion and cover.

7. A cochlear implant headpiece as claimed in claim 6, wherein the joint comprises an ultrasonic weld.

8. A cochlear implant headpiece as claimed in claim 1, further comprising:
a magnet carried by the housing.

9. A cochlear implant headpiece as claimed in claim 1, wherein
the housing includes a plurality of latch apertures; and
the cap includes a plurality of latches.

10. A cochlear implant headpiece, comprising:
a housing including a housing microphone aperture having first and second ends;
a microphone carried within the housing and associated with the second end of the housing microphone aperture, the microphone including a microphone housing with a sound aperture, an open region defining a volume within the microphone housing, and a diaphragm with a first side facing the sound aperture and a second side facing the open region;
a membrane, having pores with volumes, positioned between the housing microphone aperture and the microphone such that at least a portion of the membrane is aligned with the housing microphone aperture; and
a cap, including a sound port and a shield over the sound port, configured to be positioned on the housing such that the sound port is aligned with the first end of the housing microphone aperture and the shield is located at the first end of the housing microphone aperture;
wherein an air volume that extends from the first end of the housing microphone aperture to the first side of the diaphragm is greater than (0.3)×(the volume of the microphone open region); and
wherein the housing and cap are configured such that they will be removably connected to one another when the cap is positioned on the housing.

11. A cochlear implant headpiece as claimed in claim 10, wherein the shield is configured to prevent passage of particles that are at least 30 microns in diameter.

12. A cochlear implant headpiece as claimed in claim 11, wherein the shield is configured to allow passage of water.

* * * * *